US006761454B2

(12) United States Patent
Lai et al.

(10) Patent No.: US 6,761,454 B2
(45) Date of Patent: Jul. 13, 2004

(54) APPARATUS AND METHOD FOR DETERMINING OBJECTIVE REFRACTION USING WAVEFRONT SENSING

(75) Inventors: Shui T. Lai, Encinitas, CA (US); Andreas Dreher, Escondido, CA (US)

(73) Assignee: Ophthonix, Inc., San Diego, CA (US)

( * ) Notice: Subject to any disclaimer, the term of this patent is extended or adjusted under 35 U.S.C. 154(b) by 106 days.

(21) Appl. No.: 10/076,218

(22) Filed: Feb. 13, 2002

(65) Prior Publication Data

US 2003/0151721 A1 Aug. 14, 2003

(51) Int. Cl.[7] .................................................. A61B 3/10
(52) U.S. Cl. ...................................... 351/216; 351/221
(58) Field of Search ................................. 351/200, 205, 351/206, 211, 212, 216, 219, 221, 246, 247

(56) References Cited

U.S. PATENT DOCUMENTS

| | | | | |
|---|---|---|---|---|
| 4,105,302 A | * | 8/1978 | Tate, Jr. | ....................... 351/210 |
| 4,711,576 A | | 12/1987 | Ban | |

(List continued on next page.)

FOREIGN PATENT DOCUMENTS

| | | |
|---|---|---|
| EP | 1 153 570 A1 | 11/2001 |
| WO | WO 92/01417 | 6/1992 |
| WO | WO 98/27863 | 7/1998 |
| WO | WO 00/10448 | 3/2000 |
| WO | WO 00/19885 | 4/2000 |
| WO | WO 01/47449 | 7/2001 |
| WO | WO 01/058339 A3 | 8/2001 |
| WO | WO 01/82791 | 11/2001 |
| WO | WO 01/89424 | 11/2001 |
| WO | WO 02/09579 | 2/2002 |
| WO | WO 02/19901 | 3/2002 |
| WO | WO 02/28272 | 4/2002 |
| WO | WO 02/30273 | 4/2002 |
| WO | WO 03/009746 A1 | 2/2003 |

OTHER PUBLICATIONS

Junzhong Liang et al., *Objective measurement of wave aberrations of the human eye with the use of a Hartmann–Shack wave–front sensor*, Journal of Optical Society of America, vol. 11, No. 7, Jul. 1994, pp. 1949–1957.

Brian A. Barsky et al., *Incorporating Camera Models, Ocular Models, and Actual Patient Eye Data for Photo–Realistic and Vision–Realistic Rendering*, Fifth Int'l. Conf. on Mathematical Methods for Curves and Surfaces, Oslo, Jun. 29, 2000, "Mathematical Methods in CAGD," Vanderbilt University Press, Nashville, 2001 pp. 1–10.

(List continued on next page.)

*Primary Examiner*—Dennis W. Ruhl
*Assistant Examiner*—John R. Sanders
(74) *Attorney, Agent, or Firm*—Knobbe, Martens, Olson & Bear, LLP

(57) ABSTRACT

An apparatus for determining the objective refraction of a patient's eye includes a transparent window and a wavefront measurement device that determines aberrations in a return beam from the patient's eye after the beam passes through a corrective test lens in the apparatus. The wavefront measurement device outputs an instant display representative of the quality of vision afforded the patient through the test lens. The display can be a representation of a Snellen chart, convoluted with the optical characteristics of the patient's vision, an overall quality of vision scale or the optical contrast function, all based on the wavefront measurements of the patient's eye. The examiner may use the display information to conduct a refraction examination and other vision tests without the subjective response from the patient.

27 Claims, 5 Drawing Sheets

U.S. PATENT DOCUMENTS

| | | | |
|---|---|---|---|
| 5,062,702 | A | 11/1991 | Bille |
| 5,080,477 | A | 1/1992 | Adachi |
| 5,164,750 | A | 11/1992 | Adachi |
| 5,528,321 | A | 6/1996 | Blum et al. |
| 5,777,719 | A | 7/1998 | Williams et al. |
| 5,929,970 | A | 7/1999 | Mihashi |
| 5,949,521 | A | 9/1999 | Williams et al. |
| 5,963,300 | A * | 10/1999 | Horwitz ............ 351/209 |
| 6,007,204 | A | 12/1999 | Fahrenkrug et al. |
| 6,050,687 | A | 4/2000 | Bille et al. |
| 6,086,204 | A | 7/2000 | Magnante |
| 6,095,651 | A | 8/2000 | Williams et al. |
| 6,112,114 | A | 8/2000 | Dreher |
| 6,120,150 | A | 9/2000 | Sarver et al. |
| 6,155,684 | A | 12/2000 | Bille et al. |
| 6,199,986 | B1 | 3/2001 | Williams et al. |
| 6,234,631 | B1 | 5/2001 | Sarver et al. |
| 6,256,098 | B1 | 7/2001 | Rubenstein et al. |
| 6,257,723 | B1 | 7/2001 | Sarver et al. |
| 6,270,221 | B1 * | 8/2001 | Liang et al. ............ 351/221 |
| 6,271,915 | B1 | 8/2001 | Frey et al. |
| 6,299,311 | B1 | 10/2001 | Williams et al. |
| 6,305,802 | B1 | 10/2001 | Roffman et al. |
| 6,309,068 | B1 * | 10/2001 | Kohayakawa ............ 351/221 |
| 6,338,559 | B1 | 1/2002 | Williams et al. |
| 6,379,005 | B1 | 4/2002 | Williams et al. |
| 6,379,008 | B1 * | 4/2002 | Chateau et al. ............ 351/247 |
| 6,382,795 | B1 | 5/2002 | Lai |
| 6,394,605 | B1 | 5/2002 | Campin et al. |
| 6,396,588 | B1 | 5/2002 | Sei |
| 6,460,997 | B1 * | 10/2002 | Frey et al. ............ 351/211 |
| 6,499,843 | B1 | 12/2002 | Cox et al. |
| 6,550,917 | B1 * | 4/2003 | Neal et al. ............ 351/221 |
| 6,554,429 | B1 * | 4/2003 | Campin et al. ............ 351/211 |
| 6,607,274 | B2 * | 8/2003 | Stantz et al. ............ 351/221 |
| 2001/0033362 | A1 | 10/2001 | Sarver |
| 2001/0035939 | A1 | 11/2001 | Mihashi et al. |
| 2001/0041884 | A1 | 11/2001 | Frey et al. |
| 2002/0047992 | A1 | 4/2002 | Graves et al. |
| 2002/0122153 | A1 * | 9/2002 | Piers et al. ............ 351/212 |
| 2002/0140902 | A1 | 10/2002 | Guirao et al. |
| 2002/0167643 | A1 | 11/2002 | Youssefi |
| 2002/0186346 | A1 | 12/2002 | Stantz et al. |
| 2002/0196412 | A1 | 12/2002 | Abitbol |
| 2003/0011745 | A1 | 1/2003 | Molebny et al. |

OTHER PUBLICATIONS

Hiroshi Ohba et al., *Wavefront Sensor Using a 2–Dimensional Diffraction Grating*, Japanese Journal of Applied Physics, vol. 37, 1998, pp. 3749–3753.

Patrick P. Naulleau et al., *Extreme ultraviolet carrier–frequency shearing interferometry of a lithographic four–mirror optical system*, J. Vac. Sci. Technol. B, vol. 18, No. 6, Nov./Dec. 2000, pp. 2939–2943.

Helen L. Kung, *Micro–optical wavelength detectors*, http://clynlish.stanford.edu/~hlkung/research.html, printed Jun. 9, 2003, 3 pages.

SPIEWeb Scholarly Journals, *Optical Engineering*, vol. 38, No. 12, Dec. 1999, http://www.spie.org/web/journals/oe/oedec99.html, printed Jun. 9, 2003, 8 pages.

U.S. patent application No. 10/014,037 filed Dec. 10, 2001 (OPH.002A).

U.S. patent application No. 10/314,906 filed Dec. 9, 2002 (OPH.002CP1).

Platt et al., "History and Principles of Shack–Hartmann Wavefront Sensing," Journal of Refractive Surgery, vol. 17, Sep./Oct. 2001.

* cited by examiner

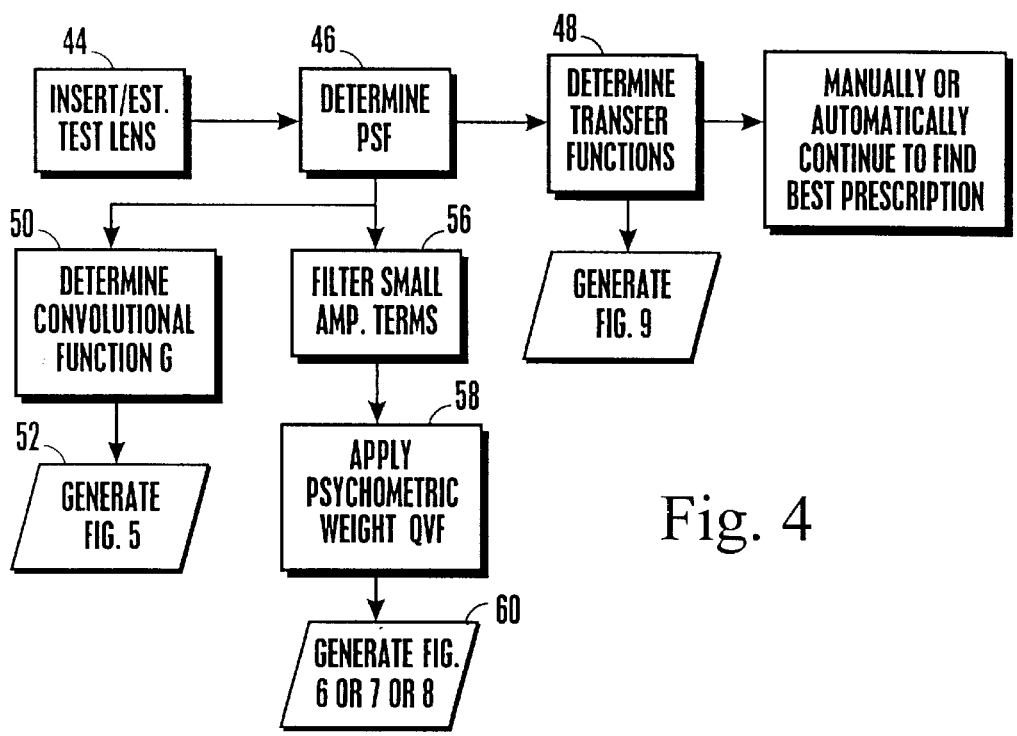
Fig. 4
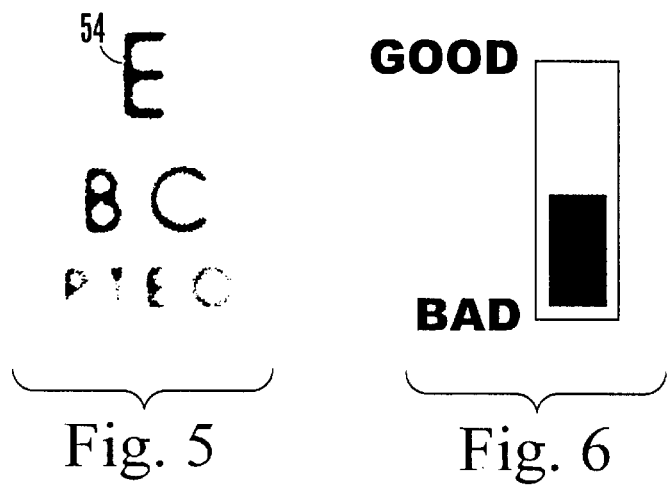
Fig. 5  Fig. 6
Fig. 7
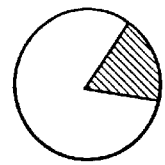

APPARATUS AND METHOD FOR DETERMINING OBJECTIVE REFRACTION USING WAVEFRONT SENSING

FIELD OF THE INVENTION

The present invention relates generally to methods and apparatus for determining a person's visual characteristics, and more particularly to apparatus for determining the refraction of the eye.

BACKGROUND

Phoropters are apparatus used by optometrists to determine a patient's visual characteristics, so that proper eye diagnoses can be made and eyewear can be prescribed. In conventional phoropters, a patient looks through the phoropter, in which various test lenses are disposed, at a target eye chart, referred to as a "Snellen chart", while an optometrist moves the test corrective lenses into the patient's field of view. In some applications, the target may be positioned at a predetermined distance from the patient. The patient is then asked to verbally compare the quality of the perceived image as afforded by one lens versus the prior lens presented. The optometrist takes note of either an improvement or a deterioration in the patient's vision through such lenses. Systematically, the test progresses towards the "best" test lens entirely based on the patient's responses. The lens parameters are then used as the basis for a prescription for eyewear.

Unfortunately, as recognized herein the patient can become fatigued during the process and/or misjudge the vision afforded by the various lenses. This can lead to the selection of a less than optimum prescription. Moreover, some patients, such as a very ill or a very young patient, might not be capable of articulating the quality of vision the various lenses afford the patient.

Objective methods of determining the patient's refraction errors have been proposed, but these other methods introduce further complications that are not present when using phoropters. In a retinoscopy method, for example, a streak of light is projected to a patient's retina, and the characteristics of the reflected light at the patient's corneal plane is analyzed to determine whether the patient is myopic, or hyperopic, and with or without astigmatism. However, the method does not provide sufficient accuracy for prescribing spectacle lenses. Consequently, its measurement results are typically used only as a starting point of a standard phoropter measurement.

Another objective measurement instrument for determining refractive errors is an autorefractor, which, owing to its speed of use, is more popular than retinoscopy. To use the autorefractor, a patient is asked to look inside an enclosed box that is part of the autorefractor. A target image is optically projected into patient's eye, and a series of lenses is automatically moved into position of the patient's line of sight to the target, to neutralize the patient's refractive errors (autorefraction). Unfortunately, the measurement outcome often differs from the patient's ideal prescription. Accordingly, like retinoscopy, autorefractor outcomes typically are used only as starting points for standard phoropter measurements.

Moreover, both retinoscopy and autorefraction fail to account for the accommodation effect of the patient, that is, for the propensity of a patient to alter his or her focus or sight to make the best of the vision test. An autorefractor measurement essentially is a snapshot of the patient's vision at a particular instant at which the autorefractor has identified a so-called neutralization point, and at this point if it happens that the patient focuses his vision for seeing an image at a distance other than what is intended, or if the patient is momentarily looking elsewhere other than the target, the output of the autorefractor is erroneous. Such deceptive focussing on the part of the patient can arise because the patient is conscious of the working distance inside the box, and when an image of an object presented to the patient which is modelled to be located at, e.g., twenty feet, the patient automatically focusses for an image at a much closer distance, knowing the actual size of the box. Examination results that include patient accommodation effects are inaccurate for prescribing spectacle lenses.

Another limitation of the autorefractor is that the examiner has no control over which lens is to be used in test. The result is that repeated measurements are likely to provide different results for the same eye from the same patient, which results in laborious and time consuming tests and retests when using the device to finalize a prescription. The present invention, having made the above-noted critical observations, provides the solutions disclosed herein.

SUMMARY OF THE INVENTION

A phoropter includes plural test lenses that can be disposed into a line of sight defined between a patient and a target, such that a patient looking at the target perceives light from the lens. A wavefront measurement apparatus is positioned to detect aberrations in light returning from the patient. The aberrations are caused by the eye of the patient.

In a preferred embodiment, the wavefront measurement apparatus includes a light source, such as a laser, for generating the light and a light detector that outputs a signal representative of the aberrations. Also, the apparatus includes a processor that receives the signal from the light detector and outputs a diagnostic signal representative thereof. The diagnostic signal is useful for generating an image representative of the test object, and/or for generating at least one visual display representative of an effectiveness of the lens in correcting a patient's vision. The visual display can include a bar chart, a pie chart, and/or a line chart, and it can be color coded.

In another aspect, a method for indicating the quality of a patient's vision includes providing a device through which a patient can look at a target. The method also includes directing a laser beam into the eye of a patient when the patient looks at the target, and then detecting aberrations in a wavefront of the light beam as the light beam returns from the patient's eye. Based on the wavefront, the method indicates a quality of a patient's vision.

In still another aspect, a method for indicating the quality of a patient's vision includes providing a device into which a patient can look, and that generates an instantaneous visual indication of a quality of a patient's vision.

In yet another aspect, a device for aiding a practitioner in knowing the integrated effect of a patient's eye and a test lens placed in front of the eye includes means for sensing a wavefront of light returning from the eye through the lens. Means are coupled to the wavefront sensing means for generating an indication of the integrated effect of the eye and the test lens.

In another aspect, a device for generating an indication of the quality of vision of a patient viewing a target includes a light beam generator directing light into the eye of the patient, and a wavefront sensing device detecting the wavefront in light returned from the eye of the patient while the patient is looking at the target. A computing device receives input from the wavefront sensing device that is representative of the wavefront. The computing device outputs a continuous update of at least one of: a point spread function, and a modular transfer function, while the patient is looking at the target. A display device displays at least one of: a simulated image of the target at the patient's retina, a quality of vision indicator indicating the quality of vision, and a graph indicating a contrast function of the patient, based at least in part on at least one of the point spread function and the modular transfer function.

In yet another aspect, a vision quantifying device includes a beamsplitter through which a patient can look at a target. A source of light emits light into an eye of the patient, which reflects from the eye as a return beam. A processor receives a signal representative of a wavefront of the return beam and generates at least one signal in response thereto, and a display receives the signal and presents a visual indication of the patient's sight.

Another aspect of the device is to provide automatic refraction process. The patient looks at a target, a test lens is positioned between the target and the patient's eye, and in the line of sight of the patient. A light beam is directed through the test lens and into the patient's eye. Using a portion of that light reflected from the surfaces within the eye a wavefront profile is reconstructed. From the reconstructed wavefront profile, A quality vision factor ("QVF") may be calculated. In order to improve the accuracy of the measurements of the patient's eye, a number of measurements of the returning wavefront profile are taken, and the corresponding QVF values for each of the measurements for that particular test lens, is analyzed. The analysis of this data provides for a determination that the correction with that particular lens is optimal. If the correction is not optimal, a next test lens is selected, and the process is then repeated the next test lens after it is positioned by mechanical means in the patient's line of sight. On the other hand, if the correction with that particular lens is optimal, than the process ends and resulting in the proper refractive correction having been identified.

The details of the present invention, both as to its structure and operation, can best be understood in reference to the accompanying drawings, in which like reference numerals refer to like parts, and in which:

BRIEF DESCRIPTION OF THE DRAWINGS

FIG. 4 is a flow chart of the presently preferred logic;

FIGS. 5–9 are exemplary non-limiting diagrams of quality of vision displays.

DETAILED DESCRIPTION OF THE PREFERRED EMBODIMENT

Figures 1, 2:
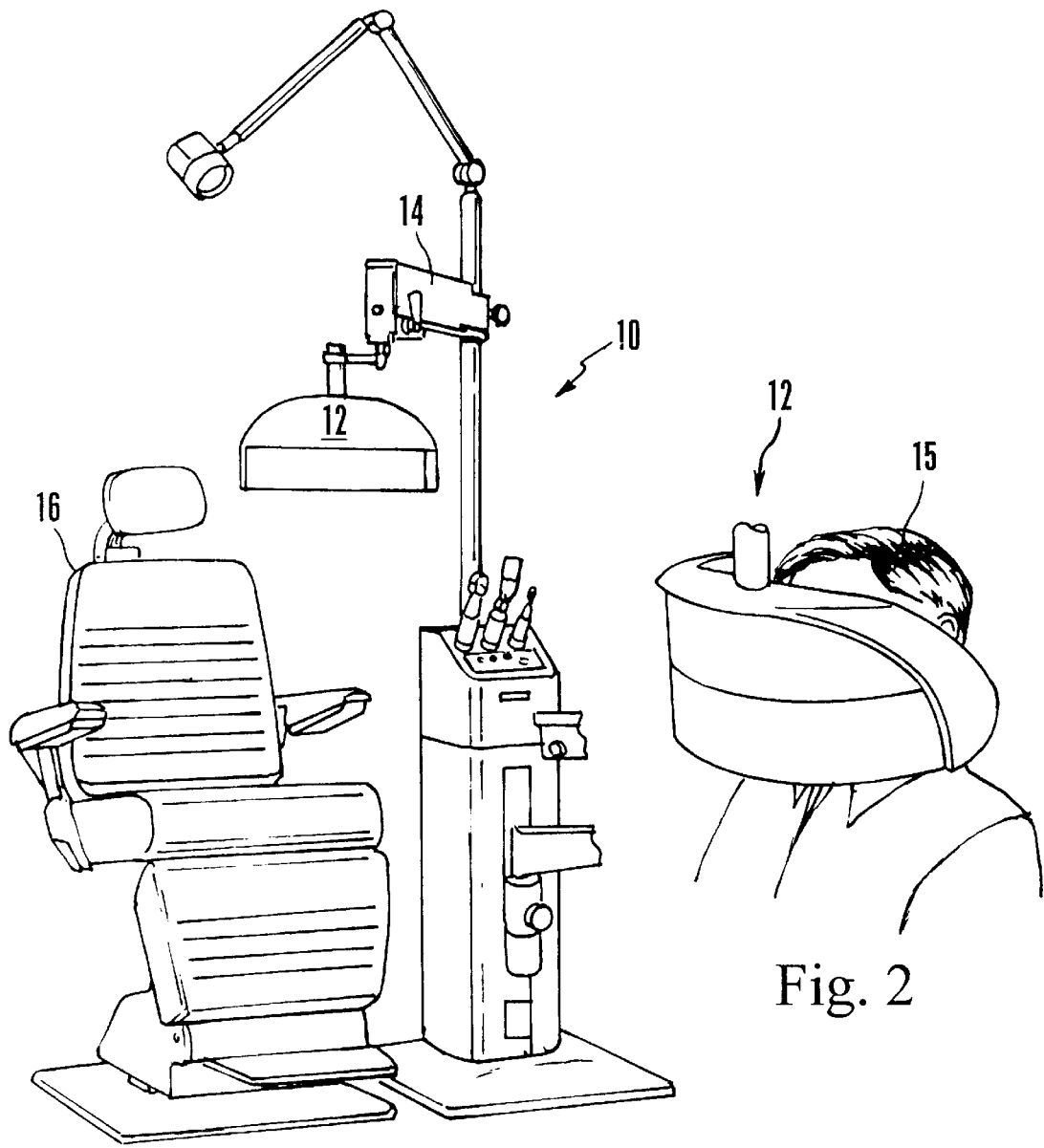
FIG. 1 is a perspective view of the present apparatus, in one intended environment.
FIG. 2 is a perspective view of the apparatus, showing a patient in phantom.

Referring initially to FIGS. 1 and 2, an apparatus of the present invention is shown, generally designated 10, and includes a housing 12 that can be mounted on a movable stand 14 for positioning the housing 12 in front of a patient 15 who might sit in an examination chair 16. As can be appreciated in cross-reference to FIGS. 1 and 2, the patient 15 can position his or her head against the housing 12. Alternatively, the housing 12 can be supported on the head of the patient 15 and/or be suspended from a flexible overhanging arm which may be attached to a stand, to provide weight balance and to facilitate mounting and dismounting of the head mounted-apparatus. Or, the apparatus of the present invention can be co-mounted with a conventional phoropter (not shown), in which case the test lenses of the present invention can be established by the lenses of the conventional phoropter.

Figure 3:
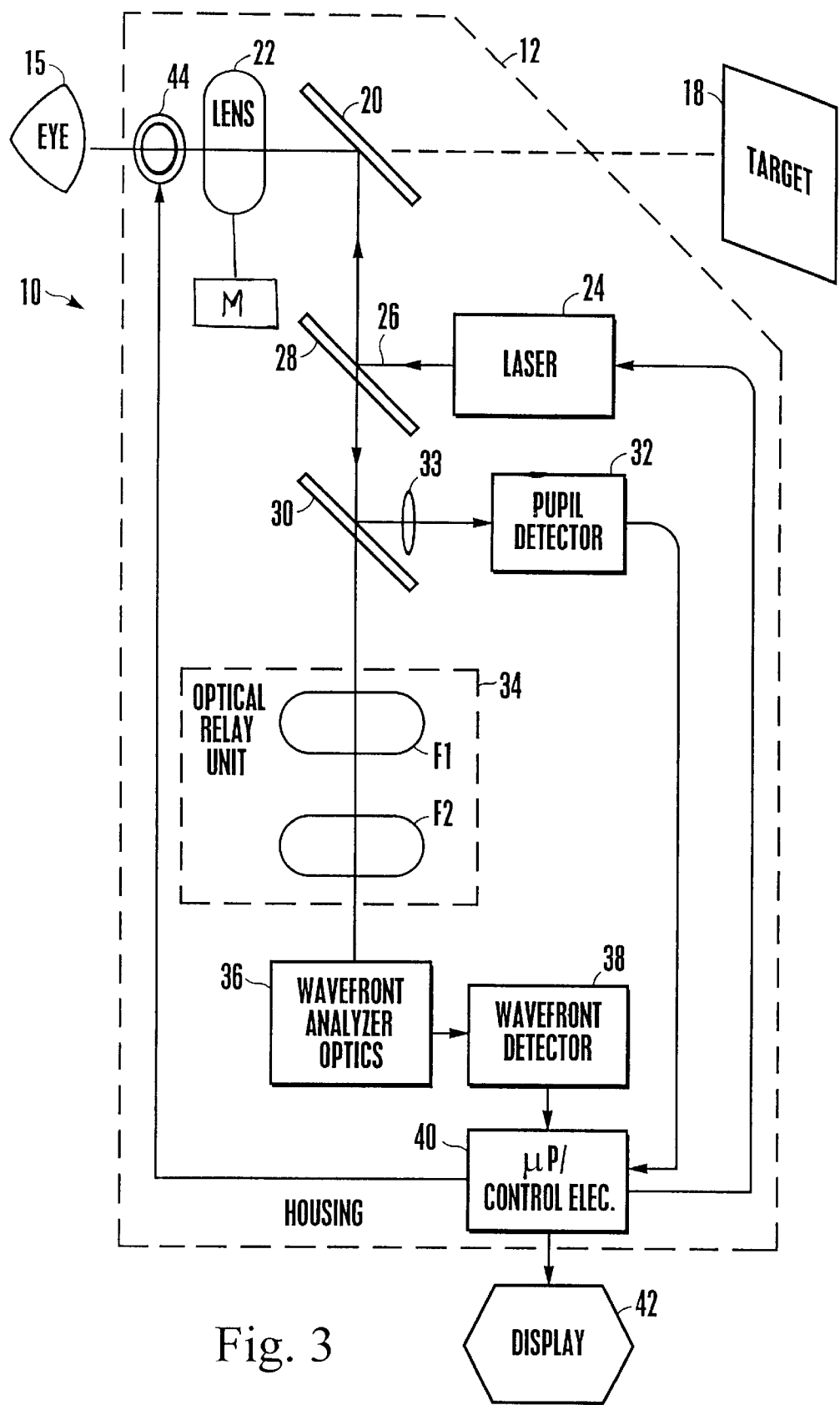
FIG. 3 is a block diagram of the components of one preferred apparatus.

Now referring to FIG. 3, the patient 15 can look through the housing 12 to a target 18, such as but not limited to a Snellen chart. The target 18 can be positioned at any appropriate distance from the patient 15, e.g., twenty feet or closer. Since the target 18 can be positioned at a distance that actually is the distance intended, the above-noted patient accommodation effects related to autorefractors, are reduced or eliminated.

FIG. 3 shows one exemplary implementation of the housing 12. While FIG. 3 shows that various components are located inside the housing 12 and various other components such as the output display is located outside the housing 12, it is to be understood that the principles advanced herein apply to phoropter systems having multiple housings, or a single housing.

In the embodiment shown, the patient looks at the target 18 through a transparent window within the housing 12, such as can be established by a primary beamsplitter 20. Interposed in the line of sight of the patient 15 are one or more movable test, or test lenses 22. By "movable" is meant physically movable by hand or computer-controlled mechanism "M" as indicated as M in FIG. 3, and more fully disclosed below to be selectively interposed within or without the line of sight of the patient 15, or movable in the sense that a variable focal length lens can be used, with its optical characteristics being variable in accordance with principles known in the art, for example those utilized in various designs of autorefractors. That is, the test lens 22 can be, but not limited to, a single concave convex lens, or a combination of optical components, including a cylindrical lens and a prism.

As also shown, a light source such as but not limited to a laser 24 generates a light beam 26 that can be directed, in one preferred embodiment, toward a laser beamsplitter 28. The laser beamsplitter 28 reflects the light beam 26 toward the primary beamsplitter 20, which in turn reflects the beam through the test lens 22 and onto the eye of the patient.

The beam 26 is then reflected by the eye of the patient 15, back through the lens 22, and is reflected off the primary beamsplitter 20. The beam passes through the laser beamsplitter 28, and a portion of the beam is reflected off a pupil detection beamsplitter 30 toward a pupil light detector 32 through one or more focussing lenses 33, for purposes to be shortly disclosed. A portion of the return beam passes through the pupil detection beamsplitter 30 and propagates through an optical relay unit 34, which focusses the beam onto a wavefront analyzer optics 36. The wavefront analyzer optics 36 generates a signal representative of the wavefront of the return beam, and a wavefront detector 38 transforms the signal into an electrical signal for analysis by a processor 40. In one preferred embodiment, the processor 40 can be associated with control electronics known in the art for undertaking control of one or more components (e.g., the light source 24) of the system 10 as more fully set forth below. Also, the processor 40 can generate the below-described visual indications of the patient's vision as corrected by the test lens 22 and can cause the indications to be displayed on a display 42, such as a video monitor, that can be mounted on the housing 12 or apart therefrom. Or, the display 42 can be a liquid crystal display that can be mounted on the housing 12 of the system 10, or a standalone display unit conveniently located for the examiner's viewing. Suitable displays may include, but not be limited to, numerical and/or graphical representations indicative of the patient's quality of vision, more details are provided in the following.

If desired, an illumination light 44, e.g., a ring-shaped fiber optic, can be mounted on the housing 12 and can be connected to the processor 40 to control the pupil size of the patient 15. The illumination light 44 can be a source of diffused light. The light intensity of the illumination light 44 is controlled by the processor 40 in response to feedback from the pupil light detector 32, which can comprise a CCD camera, or reticon detector arrays to monitor the size of the pupil, so that a predetermined pupil size can be maintained for the patient during the measurement. The locations of the pupil detection unit, including the components, beamsplitter 30, lens 33, and pupil light detector 32 can be in other appropriate locations along the optical path of the return light from the eye, including locations inside the optical relay unit 34.

As a further improvement to the accuracy of the refraction measurement, the system also monitors the first Purkinge image, an image formed by reflection at the anterior surface of the cornea of the light beam 26. The position of this image relative to the pupil boundary is an indication of gazing direction of the patient under examination. Unless the patient has strabismus in that eye, the relative position of the First Perkinge image is a well defined bright spot, and it is typically inside the pupil boundary. Therefore, in a preferred but non-limiting embodiment, the pupil detector 32 can also function as a patient gazing monitor. In this case, the relative position of the First Perkinge image to the pupil is determine by processing of the image data from the CCD camera, for example, using data filtering, contrast enhancement, and pupil boundary determination methods known in the art.

All software processing can be done in real time in a matter of a fraction of a second. The objective of this analysis is to determine whether the patient is looking at the target, or momentarily drifting off. The information is electromagnetically transmitted to the central control unit 40. If the patient is not looking at the target, the data set from the wavefront detector unit 38 is rejected, and shall not be displayed or accumulated for data analysis.

The following comments are germane to implementation details of preferred, non-limiting embodiments. The light source 24 can be a diode laser that emits light at near infrared wavelengths. Moreover, the light detectors 32, 38 can be implemented by CCD arrays or linear reticon arrays. Further, the primary beamsplitter 20 can be coated to transmit visible light and to reflect infrared light. On the other hand, the laser beamsplitter 28 can be a polarization dependent reflector, in which case the laser light is polarized, and a quarter wave plate (not shown) is disposed in the beam path to the patient 15 such that the return beam is rotated ninety degrees (90°) upon double passing the quarter wave plate for facilitating passage thereof through the laser beamsplitter 28 toward the wavefront analyzer optics 36. Alternatively, the laser beamsplitter 28 can be plate coated for high transmission and low reflectivity at forty five degrees (45°) incident angle, such that only a small portion of the laser light is reflected into the eye, but a high percentage of the return light propagates through the laser beamsplitter 28.

Continuing with the implementation details of a preferred, non-limiting embodiment, the optical relay unit 34 can include two convex lenses F1 and F2 that together establish a telescope. The lenses F1, F2 are separated from each other by a distance equal to the sum of their focal lengths, with the focal plane of the first lens F1 being located at the front surface of the test lens 22, i.e., the surface facing the primary beamsplitter 20. The focal plane of the second lens F2 is located at the image plane of the wavefront analyzer optics 36. The purpose of the telescope structure of the relay unit 34 is to relay the wavefront at the exit surface of the test lens 22 to the image plane of the wavefront analyzer optics 36. Alternative relay optics can be used to achieve the same purpose.

With respect to the non-limiting details of the wavefront analyzer optics 36, the optics 36 can include an array of lenslets arranged as in a Shack-Hartmann wavefront sensor, an example of which can be found in page 37, "Customized Corneal Ablation The Quest for Super Vision" edited by MacRae, et. al. published by Slack Incorporated, 2001, incorporated herein by reference. Various Shack-Hartmann wavefront sensors and processors are available, for example, from commercial vendors such as Wavefront Sciences, in Albuquerque, N. Mex., Zeiss/Humphrey Instruments, in Dublin, Calif., or Bausch and Lomb, in Irvine, Calif. More preferably, the optics 36 can include ruled reticles such as those disclosed in co-pending application U.S. patent application Ser. No. 10/014,037, entitled "SYSTEM AND METHOD FOR WAVEFRONT MEASUREMENT", filed Dec. 10, 2001, incorporated herein by reference, which uses a self-imaging diffraction principle to detect the wavefront in the return beam.

Regardless of the type of wavefront analyzer optics 36 used, the processor 40 analyzes the profile of the wavefront of the light returned from the patient's eye, and quantifies the wavefront aberrations in two regimes: low order aberrations, including spherical refractive error, cylinder, and axis, and higher order aberrations, including coma, spherical aberrations and other higher order terms that can be described by Zernike polynomials. Quantitative data representing the patient's quality of vision are then graphically presented on the display 42.

Now referring to FIG. 4, an exemplary mode of operation of the present invention can be seen. The patient 15 views the target 18 through the phoropter system 10, and in particular through the transparent window that is established by the primary beamsplitter 20. At block 44 the examiner initiates the vision test by inserting a selected test lens 22 in the line of sight of the patient, or by configuring a variable focal length lens 22 to have a predetermined focal length. Inserting means either a manual positioning or positioning using a motorized means. Or, the processor 40 can select a particular lens 22 and cause it to be automatically moved in the line of sight, in accordance with disclosure below.

Proceeding to block 46, the processor 40 determines the point spread function (PSF) that is derived from using, for instance, the terms of Zernicke polynomials, which is in turn derived from the wavefront passing through the wavefront analyzer optics 36 and transformed into an electrical signal by the wavefront detector 38 at the instant when the wavefront data is acquired. The processor 40 Fourier transforms the signal from the wavefront detector 38 using the following equation:

$$PSF(x, y) = |FT(P(x, y))|^2$$

wherein FT designates a Fourier Transform calculation and P(x, y) is the spatial distribution of the wavefront profile of light with the same phase (phase front) returned at the corneal plane.

Proceeding to block 48, if desired an Optical Transfer Function (OTF) can be calculated from an inverse operation of Fourier Transform as follows:

$$OTF(f_x, f_y) = FT^{-1}(PSF(x, y)),$$

wherein $f_x$, $f_y$ are spatial frequencies in x and y directions, respectively, that are orthogonal to each other.

Moreover, a Modular Transfer Function (MTF) can be determined as the amplitude of the OTF:

$$MTF(f_x, f_y) = |OTF(f_x, f_y)|.$$

The above functions are used to generate visual indications of the quality of vision that is afforded by the test lens 22 currently being viewed by the patient 15. For instance, once the PSF is determined at block 46, the logic can flow to block 50 to determine a convolutional function G as follows:

$$G(x_{img}, y_{img}) = \int\int PSF(x-x_{img}, y-y_{img})f(x_{img}, y_{img})dx\,dy,$$

wherein $f(x_{img}, y_{img})$ is the test target 18 (FIG. 3), i.e., an ideal image function, $x-x_{img}$ is the difference in the x-dimension between each point in the PSF and the corresponding ideal point in the ideal image, and $y-y_{img}$ is the difference in the y-dimension between each point in the PSF and the corresponding ideal point in the ideal image.

The convolutional function G can be used at output state 52 to generate an appropriately blurred image, point by point, of an ideal image as affected by the imperfection of the patient's eye in combination with the lens 22. For example, when the target 18 is a Snellen chart, the ideal image function can be the letter "E" or a series of other letters, e.g., of various physical sizes as conventionally used in the various lines in the Snellen chart. FIG. 5 shows one such blurred image at 54, which can be presented on the display 42. Alternatively, the target can be a picture, and the convoluted image $G(x_{img}, y_{img})$ of the picture is blurred point by point, according to the PSF, which represents an image of the target formed at the patient's retina.

Accordingly, the letters in the simulated blurred image have the same blurring as perceived by the patient 15. In this way, the examiner can visualize the clarity and sharpness of the image as a result of the lens 22 as it is perceived by the patient 15.

Alternatively or in addition to the image shown in FIG. 5, the processor 40 can generate the displays shown in FIGS. 6–8 as follows. At block 56 the wavefront profile, as indicated by the above-mentioned linear combination of Zernike polynomials, is filtered to eliminate terms with coefficient below a threshold amplitude. Moving to block 58, a psychometric weighting factor "P" is inserted for each of the remaining Zernike terms as shown in the following. This weighting factor "P" represents the effect of the brain to discriminate objects despite certain types of ocular aberrations. For example, most people can discern a letter in a Snellen chart with a certain amount of defocus while the same amplitude of aberration in coma would not allow the same patient to discern that letter. To compensate for this, a Quality of Vision Factor (QVF) is determined as follows:

$$QVF = exp(-(\Sigma_n P_n Z_n^2))$$

wherein $P_n$ is the psychometric weight factors for the corresponding $n^{th}$ term of the Zernike polynomials, and $Z_n$ is the coefficient of the $n^{th}$ term of the Zernike polynomials in the PSF.

The psychometric weighting factors "P" can be determined by presenting a particular aberration to a normative group of people, for example, between one hundred to four hundred people, depending on the accuracy level desired and the range of the scatter value of each type of aberration measurement. The patients are presented one at a time with particular types of aberrations selected from the Zernike polynomials, and then the patients are scored for the extent of success in discerning the target, for example, by the number of letters correctly read on the Snellen chart, or other standardized vision test chart. Other scoring methods base on contrast level, standardized letter size, sine or square wave patterns can also be used as targets.

The presenting means can be an aberration plate on which a selected type of aberration has been imprinted. For example, the aberration type can be a coma, or a trefoil, having the refractive index profile as specified by the corresponding Zernike polynomial.

The relative effect of each type of aberration is tabulated for the group and averaged to obtain statistically meaningful weight factors. For most practical purposes, Zernike coefficients for terms higher then the sixth order (term number twenty nine or higher) minimally contribute to the overall aberration profile of normal eyes. The method of producing various types of aberrations with desired amplitudes according to each of the Zernike terms is set forth in co-pending U.S. patent application Ser. No. 09/875,447 filed Jun. 4, 2001, incorporated herein by reference. In the event that no data for the psychometric weight factors are available, all weighting factors $P_n$ can be set to unity.

Figure 8:
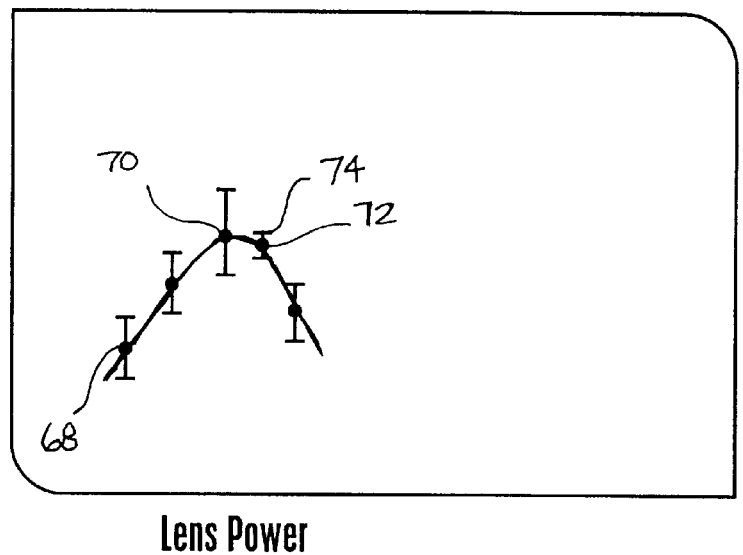

Once the QVF has been determined, one or more of the displays shown in FIGS. 6–8 can be generated and displayed as indicated in block 60. For example, as shown in FIG. 6, a bar chart display can be generated to present an overall indication of the patient's quality of vision as afforded by the lens 22 under test. As shown, the indicator can be in the form of a graduated bar 62, the height of which is proportional to the QVF determined at block 60, with zero indicating poor vision and perfect vision being indicated by a bar extending from the bottom to the top 64 of the scale. If desired, the display scale can be a log scale, in which case the "best" is indicated by the bar 62 being at zero, and rising logarithmetrically with worse vision using a root-mean-square function of the QVF. Enhancements to the bar 62 such as color-coding can be used. For instance, the bar 62 can be colored red for poor vision and green for good vision, with other colors being used to indicate intermediate qualities of vision. In lieu of the bar chart of FIG. 6, the QVF can be used to generate a pie chart as shown in FIG. 7, with the size of a pie slice 66 relative to the entire circle being linearly or logarithmetrically proportional to the QVF.

The system 10 can continuously measure the wavefront profile of the light beam returned from the patient's eye. Accordingly, in one preferred, non-limiting embodiment, a sequence of QVF measurements (e.g., twenty) for a single test lens 22 can be made in a second or two and grouped together.

As described earlier, the measurement accuracy can be improved by monitoring the gazing direction of the patient, and the computing device in block 40 can reject the data points acquired when the patient was not looking at the designated target. Furthermore, the computing device can also accumulate data and perform calculations for average values and standard deviation for selected subsets of measurement.

FIG. 8 shows a resulting display. As can be appreciated from the exemplary embodiment shown, five lenses 22 have been tested and several QVF values obtained over a short period for each. Each group of QVF values is plotted as a respective vertical line 68 on a plot of QVF versus lens, with the length of each error bar line 68 representing the standard deviation of the measurements for that particular lens and the center of each line representing the mean QVF value. The prescription can be based not only on a high mean QVF value, as indicated at points 70 and 72, but also on a small standard deviation, as indicated by bar 74. That is, the lens corresponding to the bar 74 might be selected because its QVF values had a small standard deviation from each other and it had a high mean QVF value, even if not as high as the point 70. This recognizes that some patients prefer a lens power which may not necessarily provide the sharpest image but which does result in more comfort, since a patient does relatively little searching for the "better focus" using lenses that exhibit smaller standard deviations in the QVF. For example, a patient did not have a vision check for an extended period of time, and the required correction is more than 1.5 diopters in cylinder, for example. The patient may feel uncomfortable with the full correction as afforted by the sharpest image, rather the patient prefers a smaller amount of correction which represents improvement in his vision, yet not causing dizziness or head strains. Therefore, the present invention provides objective data based on the subjective response of the patient to a test lens set 22 presented to the patient.

Figure 9:
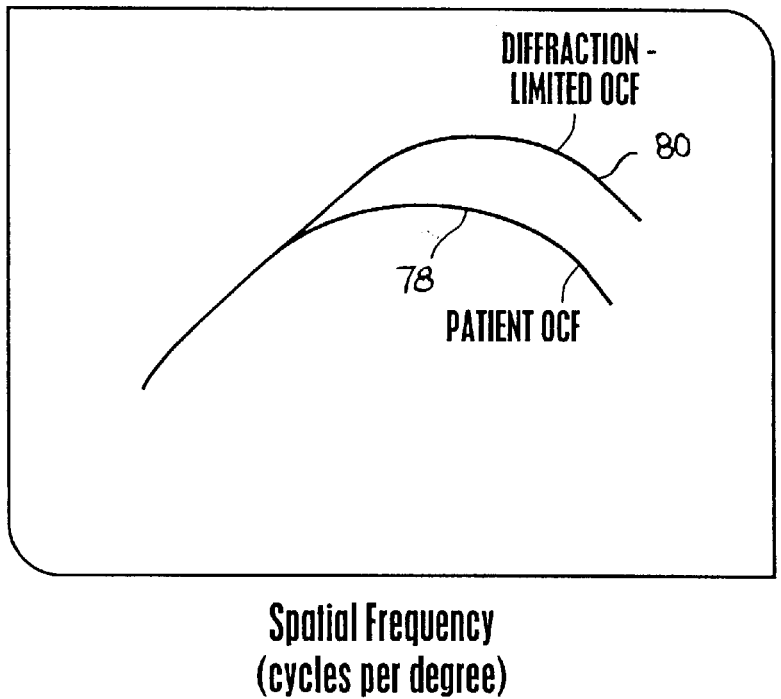

As recognized by the present invention, to diagnose a patient's contrast, the patient can be presented with a series of standardized patterns of sine wave gratings of increasing spatial frequency frequencies, with the patient offering subjective responses. The resulting examination report can be a curve that depicts a cutoff contrast intensity at various spatial frequencies. The present invention can provide a quantitative evaluation of a patient's contrast, which can be generated in addition to or in lieu of those displays disclosed above. Such a display can be generated at output state 76 in FIG. 4 and is shown in FIG. 9, showing a curve 78 depicting actual patient optical contrast function (OCF) and a reference curve 80 depicting a diffraction-limited reference. To determine OCF, the following relation is used:

$$OCF = MTF \times M_{lat}.$$

wherein MTF is the modulation transfer function determined at block 48 and $M_{lat}$ is a mathematical function accounting for the low frequency filtering of the neural system, the value of which linearly increases with spatial frequencies with a slope of unity in a log—log scale plot and reaching the maximum value of one at and above the spatial frequency of seven cycles per degree.

Accordingly, the OCF does not include the effect of the brain processing at frequencies higher than seven cycles per degree, but it does provide valuable information about the patient's ability to discern sine gratings of various spatial low frequencies based on a patient's optics.

The above process of measuring and displaying indications of the improvement in vision afforded by a particular test lens 22 to the patient 15 can be continued at block 82 until the "best" test lens is found. This can be done by the examiner manually swapping lenses 22 as in a conventional phoropter, or, as mentioned above, the positioning of test lenses 22 can be done automatically by the processor 40 controlling the moving mechanism "M", which can include a motor and coupling structure connecting the motor to one or more lenses 22, such that the mechanism follows an instruction from the processor 40 to insert the particular lens in the line of sight of the patient, as requested by the processor.

When done by the processor 40, the sequence of test lenses 22 to be used in an examination may be programmed into the processor 40 in accordance with examination strategy and routines known in the art. The starting lens can be selected based on the patient's current spectacle prescription or based on the wavefront measurement without any test lens 22 in the patient's line of sight. Consequently, in reconstructing the return beam wavefront without a test lens 22 being in the beam path, the processor 40 essentially models the uncorrected aberrations of the patient's eye in Zernike terms. Recall that the second order Zernike terms represent defocus, astigmatism and axis information. Based on the patient's pupil size and the uncorrected wavefront error amplitudes, the processor 40 can determine the equivalent diopter power in sphere and cylinder and its axis, and select the appropriate lens 22 being used to start the examination. In selecting test lenses 22, the processor 40 can use the above-disclosed QVF values in lieu of subjective responses from the patient, and can then execute the examination strategy as if it is performed with the subjective response from the patient.

Figure 10:
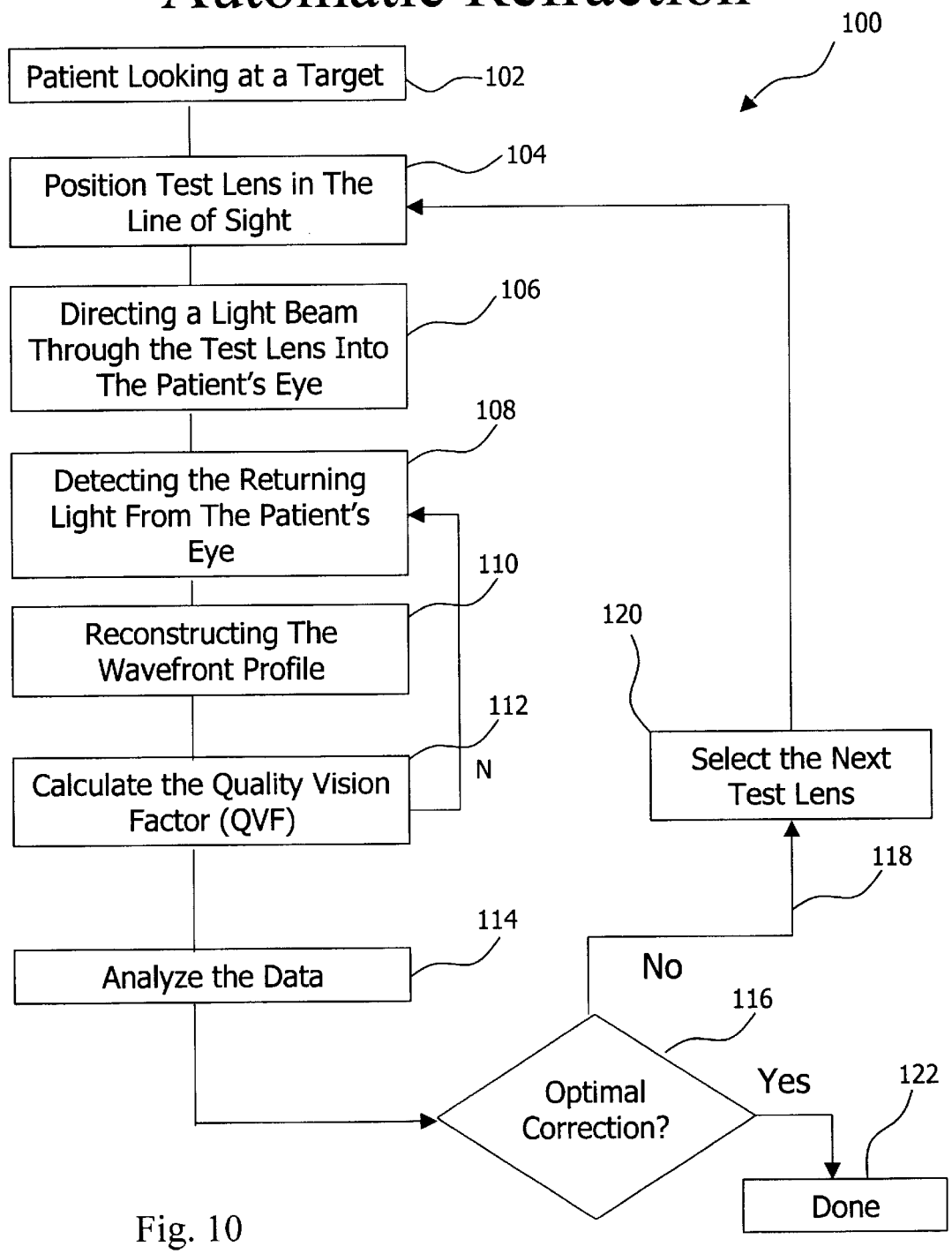
FIG. 10 is a flow chart showing the automatic refraction method of the present invention.

The automatic refraction process is depicted in FIG. 10, and generally designated 100. Process 100 begins with a first step 102 wherein the patient looks at a target. In step 104 a test lens is positioned between the target and the patient's eye, and in the line of sight of the patient. A light beam is directed through the test lens and into the patient's eye in step 106. A portion of that light is reflected from the surfaces within the eye and returns along the line of sight of the patient.

In step 108, the light returning from the patient's eye is detected. From this detected light, the wavefront profile may be reconstructed, as shown in step 110. From the reconstructed wavefront profile, the quality vision factor ("QVF") may be calculated in step 112. In order to improve the accuracy of the measurements of the patient's eye, "N" number of measurements are performed using the returning light. Thereby, "N" wavefront measurements are taken, thereby yielding N wavefront profiles and corresponding QVF values. These successive measurements are taken by returning from step 112 to step 108, in which the returning light is again detected "N" times.

Once "N" measurements have been taken and the QVF for each measurement has been calculated, the QVF for that particular test lens, is analyzed in step 114. The analysis of this data provides for a determination that the correction with that particular lens is optimal. This decision is made in step 116, and if the correction is not optimal, a next test lens is selected in step 120, and the process returns to step 104 where the next test lens is positioned in the patient's line of sight. On the other hand, if the correction with that particular lens is optimal, than the process ends in step 122 resulting in the proper refractive correction having been identified.

In a typical automatic refraction process, a series of lenses in ¼ diopters increments are used to determine the patient's optical correction. However, the present invention contemplates using more or less than the typical number of lenses, and the diopter increments can be in ⅛ instead of ¼, depending upon the magnitude of correction necessary. Also, as shown in FIG. 10, a number ("N") of measurements of the returning light are taken in steps 108 through 112 to calculate the VQF for the particular test lens. Typically, "N" will equal for example, 10–20 separate measurements being taken to provide an accurate measurement of the VQF.

However, the present invention contemplates taking more or less than the typical number of measurements depending upon the particular wavefront sensor device used, and the magnitude of correction necessary.

The prescription can be determined by a person viewing the display of FIG. 8, or automatically by the processor 40 based on a high QVF value and low standard deviation, as follows: The examiner, or the processor will examine the curve shown in FIG. 9, which connects the average values of the QVF's for various lens sets presented to the patient. An improvement may include the step of performing a best fit to the average values, suing a polynomial of up to 4 order, for example. The processor searches for the maximum value, of the "peak" of the curve. This can be accomplished by monitoring the peak value of the curve, or slope of the curve from decreasing lens power, from right to left, in FIG. 8. When the curve reaches its maximum value, the slope changes sign, and the maximum is at the zero slope value. Now, the processor send the peak value of the QVF and the corresponding lens power to the display or a printer.

Additionally, the processor also searches for the minimum value among the standard deviation in the data set as shown in FIG. 8. A figure similar to FIG. 8 showing standard deviations versus lens power can be useful (not shown) in determining the minimum value, suing the steps of a best fit curve, and search for the sign change of the slope as described above for determining the maximum QVF value. Again, this minimum standard deviation value and the corresponding lens power are sent to the display or a printer for record. For example, on the display or the printout the processor may indicate that lens power with the maximum QVF value provides for the sharpest image, while the lens power with the minimum standard deviation provides for the most comfortable prescription to the patient.

While FIG. 3 illustrates a system 10 wherein the return beam from the lens 22 is detected and analyzed and, hence, the integrated effect on the wavefront introduced by the eye and lens 22 is measured, it is to be understood that as mentioned above the return beam from the eye can also be analyzed without passing through the lens 22. In such an embodiment, the effect of the lens 22, which has a known deviation from spherical, can be accounted for by adding or subtracting the lens 22 effect as appropriate from the eye-only wavefront. To facilitate this, a sensor (not shown) can be provided that senses which lens 22 is moved into the patient's line of sight. The sensor sends a signal representative of the lens (and, hence, of the optical contribution of the lens) to the processor 40.

In any case, it may now be appreciated that if desired, the examiner can use conventional tactics in the steps of selecting test lenses 22 as if the whole process were done using a conventional phoropter that requires subjective responses from the patient. For example, the examiner can use "fogging" in accordance with principles known in the art to form an artificial image before the retina of the patient to cause the patient to relax the above-mentioned accommodative power. However, owing the present display capability of the system 10, the examiner can identify the test lens 22 with which the patient achieves good vision without accommodation, regardless of patient verbal cooperation or ability to judge and articulate which lens 22 is best. That is, by observing the present displays and continuing to decrease the focusing power of the test lenses being used and moving the image behind the patient's retina, the examiner can determine the range of accommodation of the patient.

Once the best lens 22 has been identified, the examiner may indicate this decision by pressing a "finish" button (not shown), and a printout of the examination result can be output using a printer or similar device (not shown) that is connected to the processor 40. The processor 40 may also automatically transmit via modem, internet or other appropriate means, the prescription to a remote location for lens manufacturing. A prescription to correct low order aberrations including sphere, cylinder and axis, can be used for prescribing conventional ophthalmic lenses, or a "supervision" prescription to correct all orders of aberrations can be used to prescribe improved vision lenses, such as are described in co-pending U.S. patent application Ser. No. 10/044,304, filed Oct. 25, 2001 and incorporated herein by reference.

While the particular APPARATUS AND METHOD FOR DETERMINING OBJECTIVE REFRACTION USING WAVEFRONT SENSING as herein shown and described in detail is fully capable of attaining the above-described objects of the invention, it is to be understood that it is the presently preferred embodiment of the present invention and is thus representative of the subject matter which is broadly contemplated by the present invention, that the scope of the present invention fully encompasses other embodiments which may become obvious to those skilled in the art, and that the scope of the present invention is accordingly to be limited by nothing other than the appended claims, in which reference to an element in the singular is not intended to mean "one and only one" unless explicitly so stated, but rather "one or more". All structural and functional equivalents to the elements of the above-described preferred embodiment that are known or later come to be known to those of ordinary skill in the art are expressly incorporated herein by reference and are intended to be encompassed by the present claims. Moreover, it is not necessary for a device or method to address each and every problem sought to be solved by the present invention, for it to be encompassed by the present claims. Furthermore, no element, component, or method step in the present disclosure is intended to be dedicated to the public regardless of whether the element, component, or method step is explicitly recited in the claims. No claim element herein is to be construed under the provisions of 35 U.S.C. §112, sixth paragraph, unless the element is expressly recited using the phrase "means for" or, in the case of a method claim, the element is recited as a "step" instead of an "act".

What is claimed is:

1. An apparatus for determining the refraction and aberrations of a patient's eye focused on an external physical target, comprising:

a light source;

optics directing light from said light source to the patient's eye;

a test lens having an optical power, said test lens disposable in an optical path between the patient's eye and said external physical target, such that the patient'eye looking at said external physical target receives light from said light source through the lens;

at least one wavefront measurement device positioned to detect aberrations in light returning from the patient's eye;

a housing containing said optics and said test lens, said housing having an input port and an output port, said optical path between the patient's eye and said physical target passing through said input port into said housing and through said output port thereby exiting said housing, said target being external to said housing; and processing electronics configured to compute variation in multiple wavefront measurements performed by said wavefront measurement device using said test lens having said optical power to measure a patient's subjective response to said optical power.

2. The apparatus of claim 1, wherein said housing further comprises a substantially transparent window in said optical path between the patient's eye and said external physical target through which the patient's eye views said external physical target, said window separating said optical path into a portion inside said housing and a portion of said optical path external to said housing.

3. The apparatus of claim 1, wherein the light source includes a laser for generating the light and said laser is within said housing.

4. The apparatus of claim 1, wherein the wavefront measurement device includes at least one light detector receiving a wavefront from the light returning from the patient's eye, and outputting a signal representative of the aberrations.

5. The apparatus of claim 4, further comprising at least one visual display configured to receive input from said processing electronics generated substantially instantaneously by said processing electronics using the diagnostic signal from the light detector, said processing electronics and said display configured to generate at least one data representation selected from the group consisting of (1) an image generated by a convolution of the image of the target based on the wavefront returning from the patient's eye and through the test lens; (2) a numerical and/or graphic display representative of the effectiveness of the test lens; (3) a numerical and/or graphic display of the contrast function of the patient's vision.

6. The apparatus of claim 5, wherein said processing electronics is configured to provide the visual display with representations selected from the group consisting of a bar chart, a pie chart, and a line chart.

7. The apparatus of claim 5, wherein the visual display comprises a color display and said data representation is color coded, said processing electronics being configured to provide input to said color display to create said color coded data representation.

8. The apparatus of claim 4, wherein the wavefront measurement device includes electronics that outputs a diagnostic signal substantially instantly, and wherein said diagnostic signal corresponds to the objective assessment of quality of vision.

9. The apparatus of claim 8, wherein said processing electronics is configured to generate an image representative of the target as seen by the patient's eye.

10. The apparatus of claims 9, wherein said processing electronics is configured to use said objective assessment of quality of vision to select a next lens to determine a successive objective measurement of quality of vision corresponding to said next lens.

11. The apparatus of claim 8, wherein said processing electronics is configured to use the diagnostic of signal for generating at least one visual display representative of an effectiveness of the lens in correcting a patient's vision.

12. The apparatus of claim 8, wherein said processing electronics is configured to compute the standard deviation of said objective measurement of quality of vision and one or more successive objective measurements of quality of vision and identifies an optimal vision correction lens for the patient.

13. The apparatus of claim 1, wherein said processing electronics are configured to compute the standard deviation of multiple wavefront measurements performed using said test lens having said optical power to assess a patient's subjective refraction.

14. An apparatus for determining the refraction of a patient's eye focused on a physical target, said apparatus comprising:

a light source;

optics directing light from said light source to the patient's eye, said light reflecting from a surface of said eye, said reflected light comprising a plurality of wavefronts;

a wavefront measurement device positioned along a first optical path to said eye to measure the shape of said wavefronts reflected from the patient's eye;

at least one test lens disposable along a second optical path between the patient's eye and the physical target; and processing electronics configured to determine the variation in multiple wavefront measurements that are performed by said wavefront measurement device for a fixed amount of refractive correction using said at least one test lens having said fixed refractive correction to quantify accommodation of the patient's eye, wherein said optics and said at least one test lens are arranged such that when said patient looks at said physical target through said test lens, said light from said light source is directed through said eye so as to determine said refraction from said wavefronts returning from said eye.

15. The apparatus of claim 14, further comprising a beamsplitter for merging said first optical path from said wavefront sensor to said eye and said second optical path from said eye to said physical target such that they overlap in a region between said beam splitter and said eye.

16. The apparatus of claim 15, wherein said test lens is disposed in said region between said patient's eye and said beamsplitter where said first and second optical paths overlap.

17. The apparatus of claim 14, wherein said test lens is positioned an optical path length of L from said physical target, said eye being adjusted to view said physical target said distance, L, away from said eye.

18. The apparatus of claim 17, wherein said distance between said eye and said physical target is about 20 feet.

19. The apparatus of claim 14, further comprising a housing containing said optics, said wavefront measurement device, and said at least one test lens, said housing having an input port and an output port, said second optical path between said patient's eye and said physical target passing through said input port into said housing and through said output port thereby exiting said housing, said physical target being external to said housing, wherein said housing includes a substantially transparent window disposed in said second optical path between said patient's eye and said physical target such said patient's eye can focus on said physical target, said window separating said second output path into a portion inside said housing and a portion of said second optical path external to said housing.

20. The apparatus of claim 19, wherein said light source comprises a laser and said laser is within said housing.

21. The apparatus of claim 14, wherein said wavefront measurement device includes at least one light detector receiving the light returning from the patient's eye and sending a signal to at least one processor, said at least one processor generating at least one diagnostic output based on said wavefront measurements.

22. The apparatus of claim 14, wherein said processing electronics is configured to determine the standard deviation of said multiple wavefront measurements performed by said wavefront measurement device for said fixed refractive correction to quantify accommodation of said patient's eye.

23. The apparatus of claim 14, wherein said at least one lens comprises a plurality of test lens having different amounts of refractive correction, wherein said processing electronics are configured to determine variation in multiple wavefront measurements for each of said plurality of test lens so as to quantify accommodation of the patient's eye for each of said plurality of test lens.

24. The apparatus of claim 14, wherein said at least one lens comprises an adjustable lens system having a plurality of settings that provide different amounts of refractive correction, wherein said processing electronics are configured to determine variation in multiple wavefront measurements for said different amounts of refractive correction provided by said adjustable lens system so as to quantify accommodation of the patient's eye for each of said different amounts of refractive correction.

25. The apparatus of claim 1, further comprising a housing containing said optics and said test lens, said housing having an input port and an output port, said second optical path between said patient's eye and said physical target passing through said input port into said housing and through said output port thereby exiting said housing, said physical target being external to said housing.

26. An apparatus for determining the refraction and aberrations of a patient's eye focused on a target, comprising:

a light source;

optics directing light from said light source to the patient's eye;

a test lens having an optical power, said test lens disposed in an optical path between the patient's eye and said target, such that the patient's eye looking at said target receives light from said light source through the lens;

at least one wavefront measurement device positioned to detect aberrations in light returning from the patient's eye; and processing electronics configured to determine variation in multiple wavefront measurements performed by said wavefront measurement device using said test lens having said optical power to measure a patient's subjective response to said optical power.

27. The apparatus of claim 26, wherein said processing electronics are configured to determine the standard deviation of multiple wavefront measurements performed using the test lens having said optical power to assess a patient's subjective refraction.

* * * * *